US 6,181,102 B1

(12) United States Patent
Andrews et al.

(10) Patent No.: US 6,181,102 B1
(45) Date of Patent: Jan. 30, 2001

(54) BATTERY PACK CHEMISTRY DETECTION AND IDENTIFICATION SYSTEM AND METHOD

(75) Inventors: Jonathan Neal Andrews; Gregory Dean Brink, both of McMinnville, OR (US)

(73) Assignee: Agilent Technologies, Inc., Santa Clara, CA (US)

( * ) Notice: Under 35 U.S.C. 154(b), the term of this patent shall be extended for 0 days.

(21) Appl. No.: 09/191,685

(22) Filed: Nov. 13, 1998

(51) Int. Cl.$^7$ .................................................... H02J 7/00
(52) U.S. Cl. ............................................. 320/106; 307/125
(58) Field of Search ..................... 320/106, 110; 307/125

(56) References Cited

U.S. PATENT DOCUMENTS

| | | | |
|---|---|---|---|
| D. 295,739 | 5/1988 | Lanci et al. | D13/5 |
| D. 372,456 | 8/1996 | Cooper et al. | D13/108 |
| D. 375,482 | 11/1996 | Andrews | D13/103 |
| 5,111,148 | 5/1992 | Senoo et al. | 324/433 |
| 5,183,714 | 2/1993 | Mitsui et al. | 429/123 |
| 5,200,686 | 4/1993 | Lee | 320/112 |
| 5,216,371 | 6/1993 | Nagai | 324/428 |
| 5,224,870 | 7/1993 | Weaver et al. | 439/157 |
| 5,227,262 | 7/1993 | Ozer | 429/98 |
| 5,248,927 | 9/1993 | Takei et al. | 320/113 |
| 5,350,317 | 9/1994 | Weaver et al. | 439/500 |
| 5,372,605 | * 12/1994 | Adams et al. | 607/5 |
| 5,415,947 | 5/1995 | Mitsui et al. | 429/1 |
| 5,438,248 | 8/1995 | Hyuck | 320/106 |
| 5,470,343 | 11/1995 | Fincke et al. | 607/5 |
| 5,483,165 | 1/1996 | Cameron et al. | 324/427 |
| 5,510,205 | 4/1996 | Ozer | 429/91 |
| 5,573,870 | 11/1996 | Andrews | 429/96 |
| 5,575,807 | 11/1996 | Faller | 607/5 |
| 5,602,454 | 2/1997 | Arakawa et al. | 320/106 |
| 5,604,415 | * 2/1997 | Vashi et al. | 320/106 |

(List continued on next page.)

Primary Examiner—Peter S. Wong
Assistant Examiner—Pia Tibbits

(57) ABSTRACT

A battery chemistry identification system and method that identifies the chemistry of an installed battery pack which may be one of a number of battery packs having different battery chemistries. The battery packs have electrical and physical interfaces that are functionally interchangeable. The battery packs include one or more distinguishing features in either or both aspects of the interface. The identification system includes a sensor appropriate for detecting the feature(s) and, based on the presence or absence of those distinguishing feature(s), determines which battery pack and, hence, which battery chemistry, is installed in the battery-powered device. In one particular embodiment, the system determines whether a battery installed in a battery-powered device having multiple use models is a commonly available industry standard battery pack or a customized battery pack. The industry standard battery pack has a first battery chemistry and a standard mechanical and electrical battery interface. The standard mechanical interface enables the battery pack to mechanically interoperate with an appropriately configured battery pocket while the standard electrical interface enables the battery pack to electrically interoperate with the battery pocket, typically including terminals through which energy is delivered to the device. The customized battery pack has a second battery chemistry different than the first battery chemistry and a custom interface. The custom interface includes the standard mechanical and electrical battery interfaces with the addition of one or more distinguishing feature(s). The system detects the presence or absence of the feature(s) and generates a battery chemistry indication accordingly.

18 Claims, 4 Drawing Sheets

U.S. PATENT DOCUMENTS

| | | | |
|---|---|---|---|
| 5,625,291 | 4/1997 | Brink et al. | 324/427 |
| 5,626,979 | 5/1997 | Mitsui et al. | 429/97 |
| 5,640,078 | 6/1997 | Kou et al. | 320/124 |
| 5,658,316 | 8/1997 | Lamond et al. | 607/5 |
| 5,661,392 * | 8/1997 | Imazaeki | 320/106 |
| 5,694,019 | 12/1997 | Uchida et al. | 320/106 |
| 5,710,501 * | 1/1998 | Van Phuoc et al. | 320/106 |
| 5,717,306 * | 2/1998 | Shipp | 307/125 |
| 5,717,307 * | 2/1998 | Barkat et al. | 307/125 |
| 5,721,482 | 2/1998 | Benvegar et al. | 320/106 |
| 5,729,115 | 3/1998 | Wakefield | 320/110 |
| 5,741,305 | 4/1998 | Vincent et al. | 607/5 |
| 5,742,149 * | 4/1998 | Simpson | 320/110 |
| 5,767,659 * | 6/1998 | Farley | 320/106 |
| 5,780,991 * | 7/1998 | Brake et al. | 320/106 |
| 5,780,992 * | 7/1998 | Beard | 320/106 |
| 5,850,134 * | 12/1998 | Oh et al. | 320/106 |
| 5,859,522 * | 1/1999 | Theobald | 320/106 |
| 5,867,006 * | 2/1999 | Dias et al. | 320/106 |
| 5,945,803 * | 8/1999 | Brotto et al. | 320/106 |
| 5,959,371 * | 9/1999 | Dooley | 307/130 |
| 6,008,625 * | 12/1999 | Gan et al. | 320/129 |

* cited by examiner

BATTERY PACK CHEMISTRY DETECTION AND IDENTIFICATION SYSTEM AND METHOD

RELATED APPLICATIONS

This application is related to the following commonly owned applications filed concurrently herewith, some of which disclose subject matter disclosed in the present application.

U.S. Utility patent application Ser. No. 09/191,661 entitled "Battery Vibration Control Apparatus," filed concurrently herewith, and naming as inventors Cooper et al.; and U.S. Utility patent application Ser. No. 09/192,116 entitled "System and Method for Detecting Performance Components of a Battery Pack," filed concurrently herewith, and naming as inventors Andrews et al.

BACKGROUND OF THE INVENTION

1. Field of the Invention

The present invention relates generally to battery powered devices and, more particularly, to the identification of the chemistry of a battery pack installed in such devices.

2. Related Art

Sudden cardiac arrest, i.e., a heart attack, has been attributed to over 350,000 deaths each year in the United States, making it one of the country's leading medical emergencies. World-wide, sudden cardiac arrest has been attributed to a much larger number of deaths each year. One of the most common, and life threatening, consequences of a heart attack is the development a cardiac arrhythmia commonly referred to as ventricular fibrillation. When in ventricular fibrillation the heart muscle is unable to pump an sufficient volume of blood to the body and, more importantly, to the brain. Ventricular fibrillation is generally identifiable by the victim's immediate loss of pulse, loss of consciousness and a cessation of breathing. The lack of blood and oxygen to the brain may result in brain damage, paralysis or death to the victim.

The probability of surviving a heart attack or other serious heart arrhythmia depends on the speed with which effective medical treatment is provided. There are four critical components of effective medical treatment that must be administered to a victim of sudden cardiac arrest: (1) early cardiopulmonary resuscitation to keep the blood oxygenated and flowing to the victim's brain and other vital organs; (2) early access to emergency care; (3) early cardiac defibrillation to restore the heart's regular rhythm; and (4) early access to advanced medical care. If prompt cardiopulmonary resuscitation is followed by defibrillation within approximately four minutes of the onset of symptoms, the victim's chances of surviving sudden cardiac arrest can approach or exceed forty percent. Prompt administration of defibrillation within the first critical minutes is considered one of the most important components of emergency medical treatment for preventing death from sudden cardiac arrest.

Cardiac defibrillation is an electric shock that is used to arrest the chaotic cardiac contractions that occur during ventricular fibrillation and to restore a normal cardiac rhythm. To administer this electrical shock to the heart, defibrillator pads are placed on the victim's chest, and an electrical impulse of the proper size and shape is administered to the victim in the form of an electric shock. While defibrillators have been known for years, they have typically been large and expensive making them unsuitable for use outside of a hospital or medical facility.

More recently however, portable external defibrillators for use by first responders have been developed. A portable defibrillator allows proper medical care to be given to a victim earlier than preceding defibrillators, increasing the likelihood of survival. Such portable defibrillators may be brought to or stored in an accessible location at a business, home, aircraft or the like, ready for use by first responders. With recent advances in technology, even a minimally trained individual can operate conventional portable defibrillators to aid a heart attack victim in the critical first few minutes subsequent to onset of sudden cardiac arrest.

Portable defibrillators require an energy source other than alternating current to operate in the anticipated mobile environment. Several manufacturers have provided customized battery packs for their defibrillators. More commonly, however, portable defibrillators use a standard, commonly available, rechargeable battery pack, such as those used in video camcorders. Such battery packs are generally referred to herein as industry standard battery packs. The use of industry standard battery packs allows for the easy and inexpensive purchase of replacement batteries when needed. These battery packs, while often having a standard mechanical and electrical interface, are available with different chemistries, such as lead acid, nickel cadmium (NiCd), lithium or the like.

The type of battery pack installed in a particular device depends on the anticipated operating environment in which the device is to be used. The manner in which the device is operated is commonly referred to as the "use model" of the device. Oftentimes, a battery-powered device may operate in accordance with one or more use models. In the context of battery packs, use models are defined primarily by the charge and discharge characteristics imposed on the battery pack by the device. For example, a primary factor in the performance of a battery pack is the amount of discharge experienced by the battery pack in prior uses of the device. The degree of discharge may range from a deep discharge where the energy of the battery pack is substantially depleted, to shallow discharge where an insignificant amount of energy has been depleted.

Certain battery chemistries are more suitable for certain use models than others. For instance, sealed lead acid (SLA) battery packs are ideal for supporting devices which are operated for short periods of time, each operation causing a shallow discharge of the battery pack. NiCd batteries are best suited for use in devices that are used frequently with each use being for a relatively long period of time, causing the battery pack to experience a deep discharge prior to being recharged. On the other hand, lithium (Li) battery packs are best suited for use in products that are used infrequently since they can maintain a charge for a relatively long period of time and are generally not rechargeable.

Certain battery-powered devices have a specific customer and a single use model. As a result, such devices are typically designed to operate with a single battery chemistry appropriate for that use model. Oftentimes, such devices use an industry standard battery pack.

In contrast, other devices have a variety of anticipated customers and use models. Oftentimes, such devices use a custom battery pack designed to be used specifically for the particular device. The custom battery pack is available in multiple chemistries which may be selected for the anticipated use model. For example, the LifePak 500 available from Physio-Control Corporation, Redmond, Wash., has a custom battery pack capable of being loaded with either lead acid or lithium battery cells. The battery pack having the battery chemistry appropriate to support the anticipate use model is selected and used. A drawback to this approach, however, is that the custom battery packs are expensive and not readily available.

What is needed, therefore, is a system and method to cost-effectively power portable devices that operate in accordance with more than one use model.

SUMMARY OF THE INVENTION

The present invention is a battery chemistry identification system and method that overcomes the above and other drawbacks of conventional battery pack techniques. Generally, the present invention identifies the chemistry of an installed battery pack which may be one of a number of battery packs having different battery chemistries. The battery packs have electrical and mechanical interfaces that are functionally interchangeable. In addition, the battery packs include one or more distinguishing features in either or both aspects of the battery interface. The identification system includes a sensor appropriate for detecting the feature(s) and, based on the presence or absence of the distinguishing feature(s), determines which battery pack and, hence, which battery chemistry, is installed in the battery-powered device.

Specifically, the system determines whether a battery installed in a battery-powered device having multiple use models is a commonly available industry standard battery pack or a customized battery pack. As used herein, an "industry standard" battery pack is any battery pack that generally is commonly available, whether it be due to a governmental regulation, industry-established standard, marketplace dominance or otherwise. The industry standard battery pack has a first battery chemistry and standard mechanical and electrical battery interfaces. The standard mechanical interface enables the battery pack to mechanically interoperate with an appropriately configured battery pocket to securely reside in the battery pocket. The standard electrical interface enables the battery pack to electrically interoperate with the battery pocket, typically including terminals through which energy is delivered to the device. The customized battery pack has a custom interface and a second battery chemistry different than the first battery chemistry. The custom interface includes the standard mechanical and electrical battery interfaces with the addition of one or more distinguishing feature(s). The system detects the presence or absence of the feature(s) and generates a battery chemistry indication accordingly.

Advantageously, this enables a device having multiple use models to be powered by battery packs in a cost effective manner by providing multiple custom battery packs that have interfaces interchangeable with an industry standard battery pack. The custom battery packs each have a particular battery chemistry that is different than that provided by the other customized battery packs as well as the industry standard battery pack. Selection may then be made of the battery pack that will perform optimally in the operating environment provided by the anticipated use model and, hence, most reliably supports the device during such operations.

When operating in accordance with one use model that is appropriate for a battery chemistry available in an industry standard battery pack, such a battery pack may be used. When operating in accordance with another use model that is appropriate for a battery chemistry not available in an industry standard battery pack, a customized battery pack having an interface operationally interchangeable with the industry standard battery pack can then be used. The customized battery interface provides power in the same manner as the standard electrical interface but includes or eliminates detectable features that identify it as being the customized rather than the industry standard battery pack. Thus, customized battery packs, which are commonly more expensive than industry standard battery packs, need only be used in those circumstances wherein the anticipated use model requires such a battery pack or otherwise make the use of customized battery packs preferred. This may provide significant cost benefits to the extent that the industry standard battery is used. In such circumstances, commonly available and less expensive battery packs are used, reserving the relatively more expensive and less available customized battery packs for use only when the use model requires. Further, the advantages associated with the selection of a battery pack chemistry that more reliably supports the anticipated use model cannot be overstated, particularly in portable medical devices such as portable defibrillators in which lack of such reliability can be life threatening.

Another advantage of the present invention is that it enables a manufacturer of a battery-powered device having multiple use models to avoid having to also manufacture multiple battery packs each having a battery chemistry suitable for use in the device when operating in accordance with a particular use model. Oftentimes, device manufacturers design such battery packs with proprietary or uncommon mechanical and electrical interfaces to prevent other manufactures from producing, at least initially, replacement battery packs. This is avoided with the present invention. By implementing a battery chemistry identification system that distinguishes between industry standard and custom battery packs, a battery pocket having a common design that mechanically and electrically interoperates with such industry standard battery packs may be implemented in the device. Customized battery packs having battery chemistries appropriate for specific use model(s) not supported by the industry standard battery pack may then be used with the same battery pocket. This significantly eliminates considerable development costs, resulting in a device that is economical to operate.

A still further advantage of the present invention is when the present invention is implemented in a battery-powered device that also implements a battery management system. In such devices, such as a portable defibrillator, the battery management system can then optimally manage the transfer of energy to and from (charge and discharge) and otherwise maintain the battery pack in a more efficient manner based on the battery chemistry of the installed battery pack. Other operations based on the battery chemistry can then be implemented as well. For example, if the manner in which the device is currently operated is contrary to the use model for which the battery chemistry is best suited, indications can be provided to the user. Power management systems that determine the time of battery charging cycles, the rate and amount of charge received, and other factors may also be included in the system. A number of particular aspects of the present invention are summarized below. These aspects are non-exclusive and exemplary only.

In one aspect of the invention, a battery chemistry identification system is disclosed. The identification system identifies a battery chemistry of a battery pack which may be one of a plurality of battery packs. Each battery pack has a different battery chemistry and functionally interchangeable electrical and mechanical interfaces. The use of different battery chemistries enables the device to operate in accordance with different use models. The first battery chemistry enables the industry standard battery pack to support reliable and efficient device operations in accordance with a first use model while the second chemistry enables the customized battery pack to support reliable and efficient device operations in accordance with a second use model.

Each battery pack also includes a distinguishing feature indicative of the battery chemistry of the battery pack. The distinguishing feature is included in either the mechanical or electrical interface. The identification system includes a sensor device constructed and arranged to detect the distinguishing feature and a controller operationally coupled to the sensor that determines the battery chemistry based on a presence or absence of the distinguishing feature.

In another aspect of the invention a battery chemistry identification system is disclosed. The system determines whether a battery pack installed in a battery-powered device battery pocket is a commonly available industry standard battery pack or a customized battery pack. The industry standard battery pack has a first battery chemistry and standard mechanical and electrical battery interfaces. The customized battery pack has a second battery chemistry different than the first battery chemistry and a custom interface. Along with the standard mechanical and electrical battery interfaces, the custom interface also includes one or more predetermined distinguishing features other than that provided by the standard battery interface. The distinguishing feature(s) are indicative of the different battery chemistries implemented in the customized and industry standard battery packs.

The identification system is constructed and arranged to detect a presence or absence of such feature(s) and, based on the results of this detection, generates an output indicative of the battery chemistry. Specifically, in one embodiment, the identification system includes a sensing device constructed and arranged to detect a presence or absence of the distinguishing feature(s) and a signal generating circuit electrically connected to the sensing device for generating the battery pack chemistry identification signal.

The distinguishing feature may, as noted, reside on the mechanical or electrical interface of the custom battery pack. Generally, the standard electrical battery interface comprises positive and negative terminals. The device includes corresponding contacts to electrically contact the battery pack terminals when the industry standard and customized battery packs are installed in the device. Preferably, the distinguishing features include one battery terminal on the customized battery pack having a dimension different than a corresponding battery terminal on the industry standard battery pack. This difference is not significantly great to be considered an operational difference in the electrical interface provided by the two battery packs, yet it is sufficiently different to be detectable by a third contact of the identification system. The third contact is located adjacent to the corresponding contact in the device so as to electrically detect the different terminal size. In an alternative embodiment, the distinguishing features include a third electrical terminal disposed on a surface of the customized battery pack. The sensing device in such an embodiment includes a third electrical contact disposed within the battery pocket. The third contact is constructed and arranged to contact the third electrical terminal of the customized battery pack when installed in the battery pocket.

As noted, the industry standard and customized battery packs have substantially similar mechanical interfaces. In one embodiment, the industry standard battery pack includes a recess to mate with a protrusion in a receiving battery pocket so as to secure the industry standard battery pack within a battery pocket. The customized battery pack would provide a substantially similar recess in substantially the same location. In an alternative embodiment, the third terminal is located in such a recess while the third contact is located on such a protrusion.

In a still further aspect of the invention, a battery-powered device such as a portable defibrillator is disclosed. The device has a plurality of use models each having associated therewith a characteristic power consumption time and duration. The device includes a battery pocket constructed and arranged to receive and operate with an industry standard battery pack. The industry standard battery pack has a first battery chemistry and standard mechanical and electrical battery interfaces. A customized battery pack having a second battery chemistry different than the first battery chemistry may also be used in the same battery pocket. The customized battery pack has a custom interface that includes the standard mechanical and electrical battery interfaces, as well as one or more distinguishing features indicative of battery chemistry not provided on the battery interface of the industry standard battery pack. The distinguishing feature may be located on the standard mechanical interface or standard electrical interface of the customized battery pack.

The device also includes a battery chemistry identification system constructed and arranged to detect a presence or absence of such distinguishing features. The identification system generates a battery chemistry signal indicative of the battery chemistry of a battery pack installed in the battery pocket. In one embodiment, the identification system includes a sensing device constructed and arranged to detect a presence or absence of the distinguishing feature(s). It also includes a controller operationally coupled to the sensing device for generating the battery pack chemistry identification signal based on the presence or absence of the distinguishing feature(s).

The industry standard battery packs oftentimes have lead acid as the first battery chemistry. This enables the industry standard battery pack to support reliable and efficient device operations in accordance with a first use model wherein the device is operated for short periods of time, each usage causing a shallow discharge of the installed battery pack. The customized battery pack may include a different battery chemistry as the second battery chemistry, such as lithium (Li) or nickel cadmium (NiCd). The second battery chemistry enables the customized battery pack to support reliable and efficient device operations in accordance with a second use model. The NiCd battery chemistry, for example, is best suited for use in the device when the second use model includes frequent use of the device for relatively long periods of time, causing the installed battery pack to experience a deep discharge prior to being recharged.

In a still further aspect of the invention, a customized battery pack is disclosed. The customized battery pack includes a mechanical and an electrical interface substantially the same as that provided by an industry standard battery pack, along with a battery chemistry that is different than that provided in the industry standard battery pack. The customized battery pack also includes a distinguishing feature indicative of the different battery chemistries located on either of the mechanical and electrical interfaces that is not provided on the industry standard battery interface. In one embodiment, the battery chemistry of the industry standard battery pack is lead acid while the battery chemistry of the custom battery pack is lithium. In an alternative embodiment, the battery chemistry of the industry standard battery pack is lead acid while the battery chemistry of the custom battery pack is nickel cadmium.

As noted above, the present invention provides numerous advantages. Various embodiments of the present invention provide certain advantages and overcome certain drawbacks of conventional techniques while other embodiments provide the same or different advantages and overcome the same or other drawbacks in the same or different manner. Thus, not all embodiments of the invention share the same advantages and those that do may not share them under all circumstances. Further features and advantages of the present invention as well as the structure and operation of various embodiments of the present invention are described in detail below with reference to the accompanying drawings.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps, in which the left-most one or two numerals of a reference numeral indicate the number of the figure in which the referenced element first appears, and in which.

DETAILED DESCRIPTION

The present invention is a battery chemistry identification system and method that overcomes the above and other drawbacks of conventional battery pack techniques. Generally, the present invention identifies the chemistry of an installed battery pack which may be one of a number of battery packs having different battery chemistries. The battery packs have electrical and mechanical interfaces that are functionally interchangeable. The battery packs include one or more distinguishing features in either or both aspects of the interface that are indicative of the chemistry of the battery cells included in the respective battery pack. The identification system includes a sensor appropriate for detecting such feature(s) and, based on the presence or absence of those distinguishing feature(s), determines which battery chemistry is installed in the battery-powered device.

Figure 1:
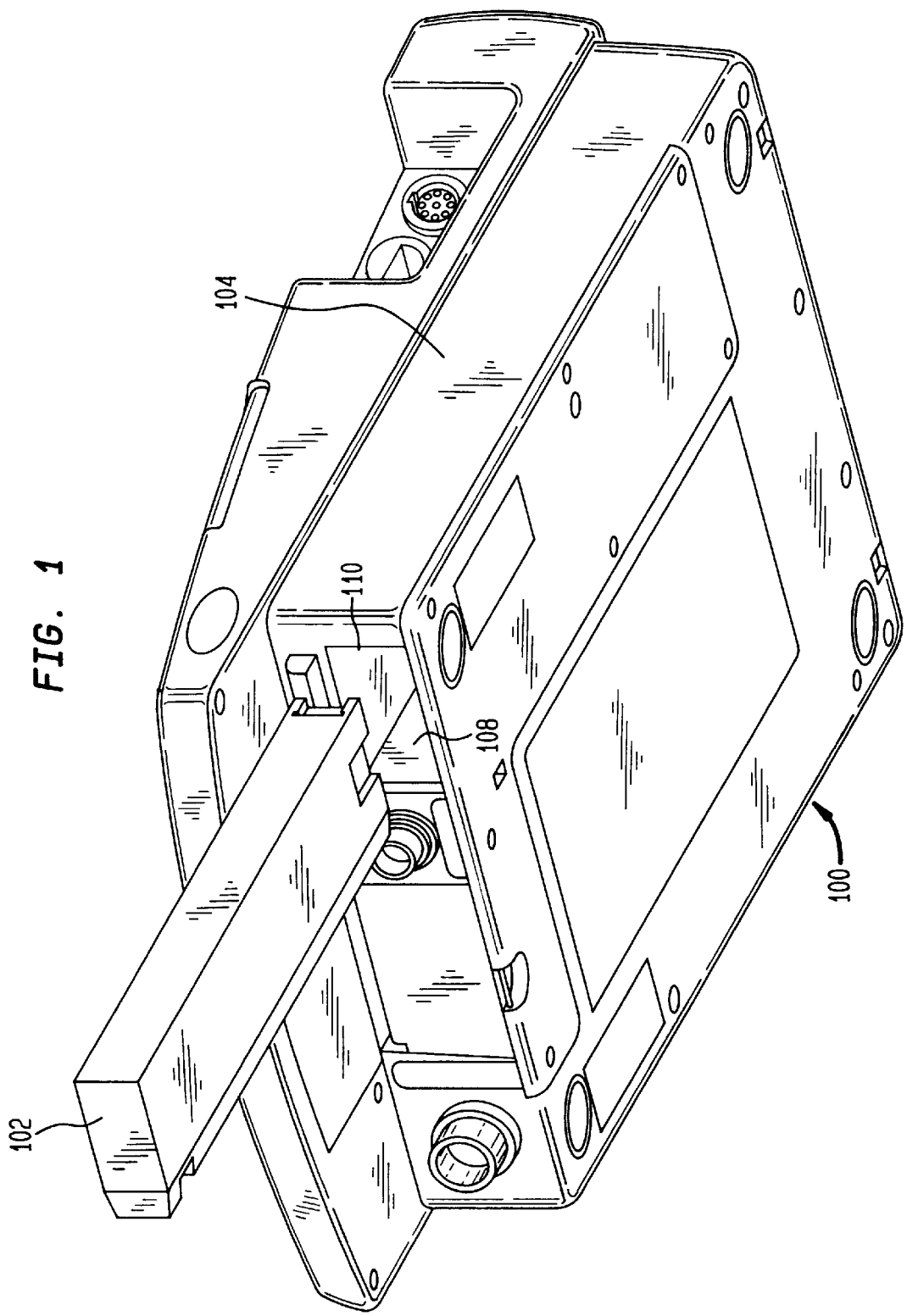
FIG. 1 is a perspective view of a defibrillator suitable for implementing one embodiment of the battery chemistry detection and identification system of the present invention.

The present invention may be implemented in virtually any battery-powered device. However, the illustrated embodiments of the present invention are shown particularly for a battery-powered defibrillator. FIG. 1 is a perspective view of one such defibrillator suitable for implementing one embodiment of the battery chemistry detection and identification system of the present invention. Portable defibrillator 100 may be, for instance, model M3500B automatic external defibrillator (AED) available from an Hewlett-Packard Company, Andover, Mass., USA.

In accordance with the present invention, defibrillator 100 may be operated in accordance with different "use models." As used herein, "use models" are defined by the time and duration and other power usage requirements placed on the battery pack by the device. The performance of an installed battery pack 102 is dependent on the amount of discharge and subsequent charge experienced by battery pack 102 during each use of defibrillator 100, as well as the time duration between uses. The degree of discharge may range from a deep discharge where the energy of the battery pack is substantially depleted, to shallow discharge where an insignificant amount of energy has been depleted.

As noted, certain battery chemistries are more suitable for certain use models than others. Three battery chemistries will be discussed herein, although it should be understood that the present invention applies to any number of battery chemistries. Lead acid battery packs are ideal for supporting defibrillator 100 when it is to be operated for short periods of time; nickel cadmium battery packs are better suited for use in defibrillator 100 when it is to be used frequently and for relatively long periods of time; and lithium battery packs are suitable for use in defibrillator 100 when it is anticipated that defibrillator 100 is to be used infrequently.

A replaceable battery pack 102 is electrically and mechanically mounted in a battery pocket 104 of defibrillator 100. As is common with many devices which utilize battery packs, battery pocket 104 includes a sleeve 108 terminating in an opening 110 through which battery pack 102 is inserted into sleeve 108.

In the illustrative embodiment, battery pocket 104 is configured to electrically and mechanically interface with an industry standard battery pack. An industry standard battery pack is one that is commonly available and, as a result, is readily available and often low in cost. The industry standard battery pack has a battery chemistry and standard mechanical and electrical battery interfaces. For example, in the illustrative embodiment, the industry standard battery pack is the Panasonic LC-TA122P sealed lead acid (SLA) battery pack commonly used in video camcorders and other consumer electronic devices.

As noted, it is preferable that the battery chemistry of battery pack 102 installed in defibrillator 100 is that which is best suited for the anticipated use model. To accommodate the different use models of defibrillator 100, customized battery packs are provided having a different battery chemistry and, in accordance with the present invention, a custom interface. The custom battery pack has functionally interchangeable electrical and mechanical interfaces with the industry standard battery pack and a different battery chemistry, such as lithium.

One use of the present invention is to select the battery pack appropriate for the anticipated use model of defibrillator 100. In one preferred embodiment, however, the reverse is implemented. That is, the use model implemented in defibrillator 100 is determined by the chemistry of battery pack 102 currently installed in battery pocket 104. It is this latter embodiment that is described below.

To determine which battery chemistry is currently installed in battery pocket 104, the custom interface on the customized battery pack includes, in addition to the standard mechanical and electrical battery interface implemented in the industry standard battery pack, one or more distinguishing features other than that provided by the standard battery interface. In accordance with the present invention, the distinguishing feature(s) are indicative of the different battery chemistries implemented in the custom and industry standard battery packs. Importantly, these distinguishing features are predetermined detectible differences that may be located at one or more locations on the battery interface and which do not interfere with the interchangeability of the electrical and mechanical interfaces of the customized and industry standard battery packs. It should become apparent from the following description that such features may be the presence or absence of any feature on either the industry standard or customized battery pack. The following description addresses two battery packs, an industry standard battery pack and one customized battery pack, for which only one distinguishing feature is required to distinguish. It should understood, however, that any number of customized battery packs necessary to support different use models of defibrillator 100 may be implemented. Additional distinguishing features would accordingly be provided.

Figure 2:
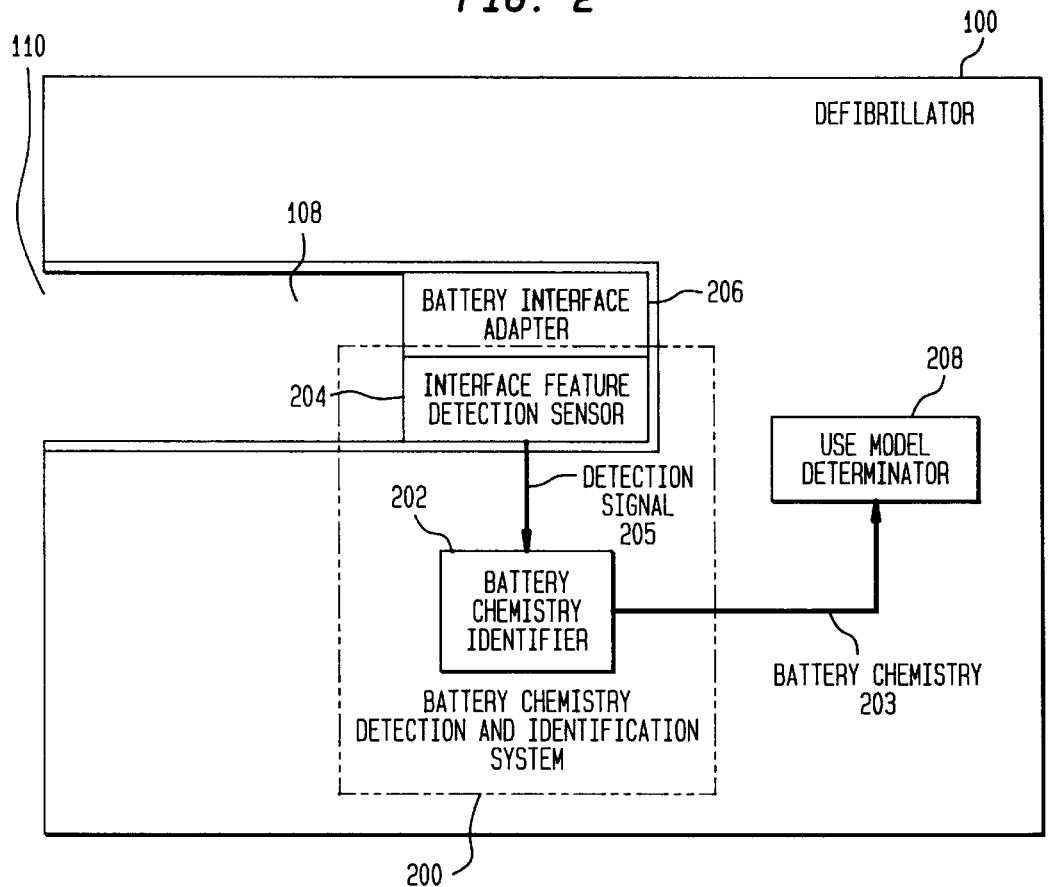
FIG. 2 is a schematic block diagram of the defibrillator shown in FIG. 1 illustrating the battery chemistry detection and identification system.

FIG. 2 is a block diagram of one embodiment of the battery chemistry detection and identification system implemented in defibrillator 100. Battery chemistry detection and identification system 200 ("system 200") primarily includes an interface feature detection sensor 204 and a battery chemistry identifier 202. Interface feature detection sensor 204, or simply sensor 204, is constructed and arranged to detect the distinguishing features on the customized and industry standard battery interfaces. Sensor 204 generates a detection signal 205 indicating which distinguishing features have been detected on the installed battery pack 102. The battery chemistry identifier 202 determines the battery chemistry of the installed battery pack 102 based on a presence or absence of the distinguishing features as set forth in the detection signal 205, and generates a battery chemistry signal 203 indicating such for use by other systems of defibrillator 100. It should be appreciated that if many customized battery packs, each with a different chemistry, are provided, then more than one distinguishing feature may be used to uniquely identify each battery pack. A corresponding increase in detection signals 205 and chemistry indicators 203 may then be implemented.

In one particular embodiment, defibrillator 100 also includes a use model determinator 208 that determines the use model that defibrillator 100 will operate based on the battery chemistry of the installed battery pack 102. That is, defibrillator 100 will automatically reconfigure certain systems to optimally draw power from and otherwise maintain installed battery pack 102, as well as to operate most reliably given the chemistry of the installed battery pack.

As shown in FIG. 2, a battery interface adapter 206 is located at an end of battery pocket 104 to electrically and mechanically interface with a battery pack 102 installed in sleeve 108. As will be described in further detail below, in the illustrative embodiment, sensor 204 is mounted in battery interface adapter 206. In one embodiment described below, battery interface adapter 206 includes a printed circuit board (PCB) on which battery chemistry identifier 202 is implemented. In such embodiments, then, the entire system 200 is implemented within battery interface adapter 206. Alternatively, detection sensor 204 could be appropriately configured to generate a sufficiently strong detection signal 205 to be received by a remotely located battery chemistry identifier 202.

It should also be understood that any means for communicating between sensor 204 and identifier 202, as well as between system 200 and other components of defibrillator 100 may be used. This may include, for example, dedicated communication lines, data buses, shared memory, or the like. The selection of such techniques and systems are considered to be well known design selections not pertinent to the present invention.

Figure 3:
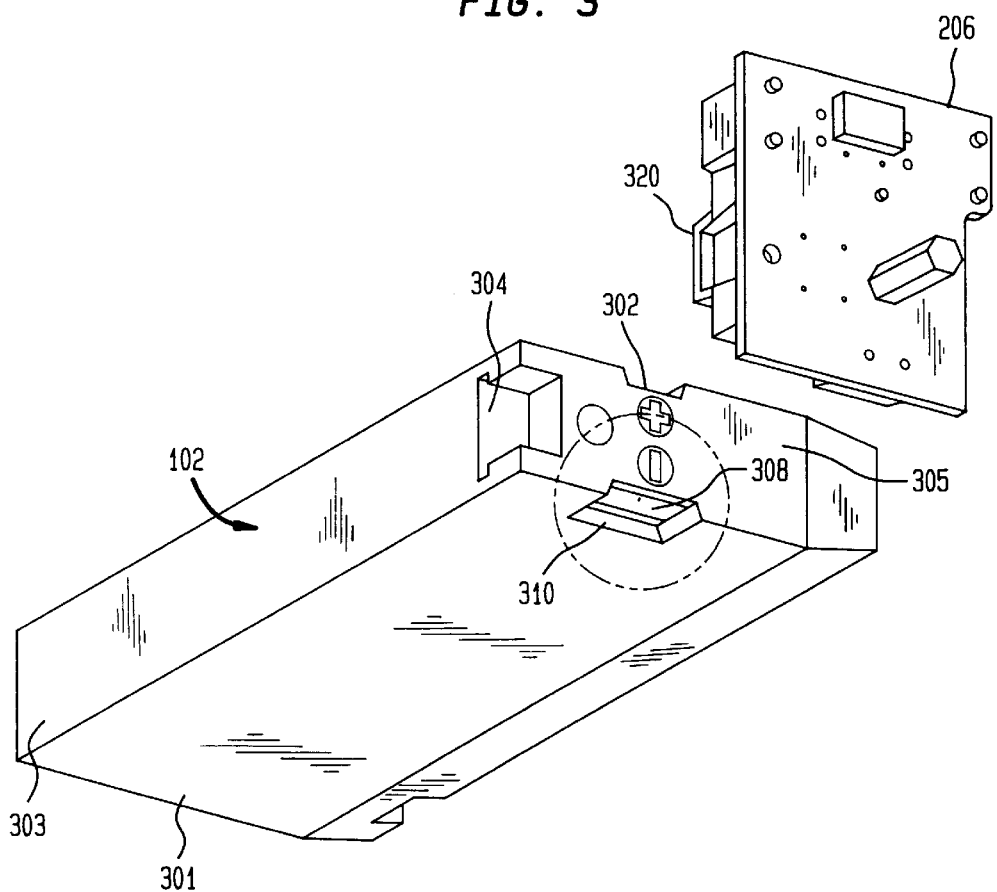
FIG. 3 is a perspective view of an exemplary industry standard battery pack and a customized battery pack implemented in accordance with one embodiment of the present invention.
Figure 3A:
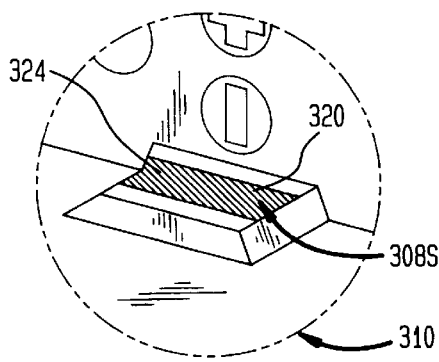
Figure 3B:
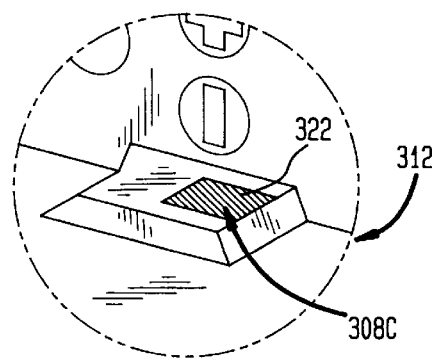

FIG. 3 is a perspective view of battery pack 102 having electrical and mechanical interfaces that mate with corresponding interfaces on battery interface adapter 206. Two magnified views are also shown in FIG. 3 to illustrate one embodiment of the distinguishing features of the present invention. The magnified view of FIG. 3A illustrates one embodiment of an industry standard battery pack 310 having the same electrical and mechanical operational interface as battery pack 102. Similarly, the magnified view of FIG. 3B illustrates one embodiment of a customized battery pack 312 having the same electrical and mechanical operational interface as battery pack 102. In addition, as will be described in detail below, the magnified views 3A and 3B illustrate the distinguishing feature detected by sensor 204 in accordance with the illustrative embodiment of the present invention. The common or interchangeable electrical and mechanical battery interfaces are first described, followed by a description of the distinguishing features shown in FIGS. 3A and 3B.

Battery pack 102 is an elongated battery pack having four elongate sides, two of which, 301, 303, are shown in the perspective view of FIG. 3. In the orientation shown in FIG. 3, side 301 is referred to as bottom side 301 and side 303 is referred to as left side 303. It follows then that the side opposite bottom side 301 (not shown) is referred to herein as the top side; while the side opposite left side 303 (also not shown) is referred to as the right side. A front end side 305 of battery pack 102 mates with battery interface adapter 206 when battery pack 102 is installed in battery pocket 104. A rear end side (not shown) of battery pack 102 is exposed to the operator through opening 110 when battery pack 102 is installed in defibrillator 100.

The interchangeable operational electrical interface is generally comprised of positive and negative terminals. Certain recesses disposed in surfaces of battery pack 102 have disposed therein battery terminals while others do not. Specifically, a recess 302 formed in the surfaces of the top side and front end side 305 houses positive terminal 306 (not shown) while a recess 310 formed in the surfaces of bottom side 301 and front side 305 houses negative terminal 308. A third recess 304 is also formed in the surface of left side 303 and front end side 305. Recesses formed in front end side 305 and another side such as sides 301 and 303 mate with properly aligned and dimensioned protrusions extending into sleeve 108 of battery pocket 104. In this illustrative embodiment, such protrusions reside on battery interface adapter 206 which, as noted, is mounted within battery pocket 104.

Referring now to the magnified views of FIGS. 3A and 3B, the distinguishing features of the illustrative embodiment will now be described. As noted, one or more distinguishing features may reside on either the mechanical or electrical interfaces. The selection of the implementation of the one or more distinguishing features may involve such considerations as the ability to be sensed easily, cost to manufacture, robustness, and ability to withstand degradation in efficacy over time. In this embodiment, the distinguishing feature is implemented in the electrical interface.

The industry standard battery pack 102 is a Panasonic Model LC-TA122P. As such, and as shown in FIG. 3A, this battery pack has a negative terminal 308S ("standard"). The operational portion of negative terminal 308S is identified by reference numeral 320. Accordingly, a region 322 having similar dimensions is provided on negative terminal 308C ("customized") to provide the same electrical interface. However, the remaining portion 324 of negative terminal 308S is not required to transfer energy and, thus, is not considered to be part of the operational electrical interface. In customized battery pack 312 shown in FIG. 3B, negative terminal 308C does not include such a region. As a result, the distinguishing feature of this embodiment of the present invention is the absence of portion 324 of negative terminal 308S on negative terminal 308C of customized battery pack 312.

This results in the distinguishing feature including one battery terminal 308C on the customized battery pack 312 having a dimension different than a corresponding battery terminal 308S on the industry standard battery pack 310. This difference is not significantly great to be considered an operational difference in the electrical interface provided by the two battery packs, yet it is sufficiently different to be detectable by a third contact (not shown) of the identification system 200.

In an alternative embodiment, the distinguishing features include a third electrical terminal disposed on a surface of the customized battery pack 312. The sensor 204 in such an embodiment includes a third electrical contact disposed within battery pocket 104 constructed and arranged to contact the third electrical terminal when the customized battery pack is installed in the battery pocket. This third electrical terminal may take on one of many forms. Similar to the embodiment illustrated in FIG. 3A, the third electrical terminal and one of the customized battery pack terminals may form a unitary terminal. In an alternative embodiment the third terminal is located in a recess, such as recess 304, while the third contact is located on such a corresponding protrusion 320.

It should be understood that an alternative embodiment of the present invention, distinguishing features and sensor 204 may be configured to use other mediums for communicating different battery chemistries. For example, in one alternative embodiment, the distinguishing features may include a reflective coating or label placed on front face 305 of customized battery pack 312. An appropriately aligned photodetector is provided as sensor 204 to detect the presence or absence of such a distinguishing feature. In still alternative embodiments, other mechanisms such as magnetics may be used. In still further embodiments, a communication port may be provided on front face 305 of customized battery pack 312 through which a circuit located in customized battery pack 312 communicates the chemistry of the battery cells in the battery pack. In such an embodiment, sensor 204 would include a receiver that receives and interprets such signals. As one skilled in the art should find apparent, any means for communicating the chemistry of the installed battery packs may be used in accordance with the present invention.

Figure 4:
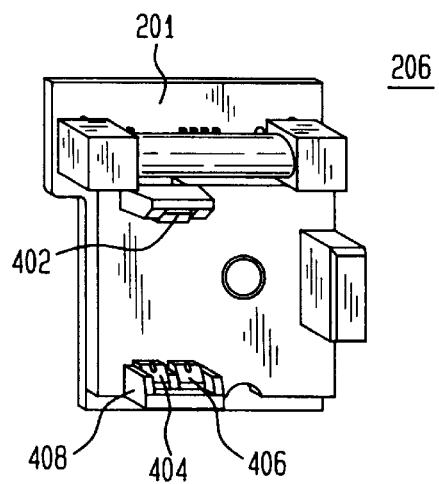
FIG. 4 is a perspective view of one embodiment of a battery interface adapter, suitable for mounting in the battery pocket shown in FIG. 1, incorporating the battery chemistry detection sensor of one embodiment of the present invention.

FIG. 4 is a perspective view of one embodiment of a battery interface adapter 206 mounted in battery pocket 104. Battery interface adapter 206 includes protrusions extending from a base 201 into battery pocket 104. In the illustrative embodiment, base 201 is a printed circuit board. These protrusions, also commonly referred to as extensions, arms and the like, are aligned with recesses 302 and 310, respectively, and are dimensioned to mate with the corresponding recess when battery pack 102 is installed in battery pocket 104. As used herein, a recess and corresponding protrusion are dimensioned such that the protrusion easily slides into the corresponding recess as battery pack 102 is installed in battery pocket 104.

In the illustrative embodiment, battery interface adaptor 206 includes a positive contact 402 constructed and arranged to electrically mate with the positive terminal of the installed is battery pack 102. Likewise, battery interface adaptor 206 includes a negative contact 404 constructed and arranged to mate with the negative terminals 308S, 308C of the industry standard battery pack 310 and customized battery pack 312, respectively. In accordance with the present invention, sensor 204 is implemented as a third electrical contact 406 on battery interface adaptor 206. This third electrical contact 406 detects the presence or absence of the region 324 on negative terminals 308S (presence) and 308C (absence). To perform such a detection, the third electrical contact 406 is positioned adjacent to negative contact 404 on the protrusion 408. In this embodiment, the detection signal 205 generated by detection sensor 204 is nothing more than either an open circuit or a ground signal. As noted, this detection signal 205 is provided to battery chemistry identifier 202. In certain embodiments, the detection signal 205 is amplified, filtered or otherwise conditioned prior to being generated.

Figure 5:
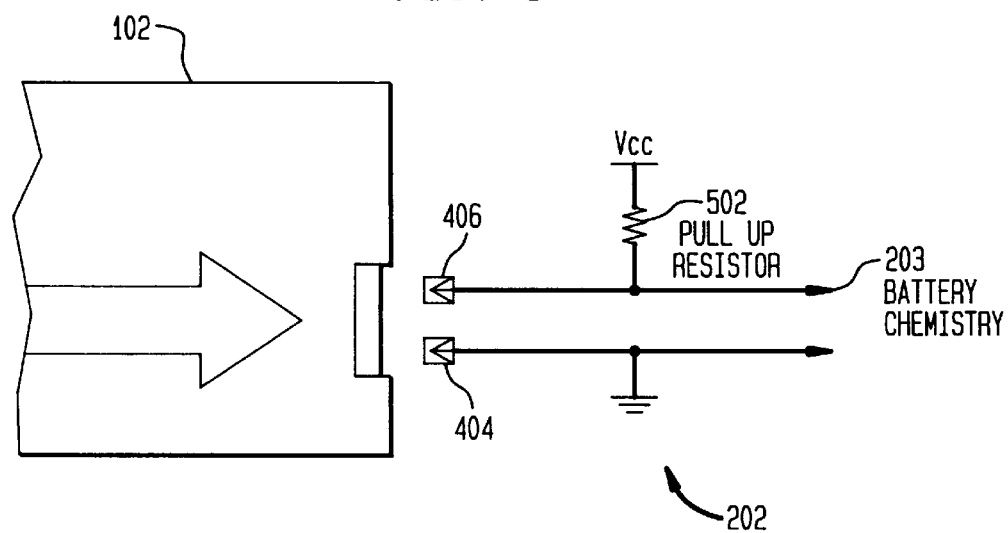
FIG. 5 is a schematic diagram of one embodiment of the battery chemistry identifier of the present invention.

FIG. 5 is a schematic diagram of battery chemistry identifier 202 which may be implemented in the illustrative embodiment of the present invention. As shown in FIG. 5, terminal 406 is connected to a voltage Vcc through a pull-up resistor 502. Grounding of contact 406 drives battery chemistry signal 203 to ground potential. Otherwise, signal 203 is held at a high voltage level. As one skilled in the relevant art should find apparent, a myriad of simple circuits may be used to receive detection and process detection signal 205. In embodiments wherein detection signal 205 contain a number of values, then appropriate circuitry would be implemented to interpret such a signal. In one preferred embodiment, a series of relays are utilized to receive a plurality of detection signals 205 generated by sensors 204 arranged so as to output a battery chemistry 203 indicative of the chemistry of one of a plurality of customized battery packs.

Having now described various embodiments of the invention, it should be apparent to those skilled in the relevant art that the foregoing are illustrative and not limiting, having been presented by way of example only. For example, it should be understood that in alternative embodiments circuits that the battery identification means could be placed on any surface of the battery for sensing by the defibrillator unit. Numerous other embodiments and modifications thereof are contemplated as falling within the scope of the present invention as defined by appended claims and equivalents thereto.

What is claimed is:

1. A battery-powered portable defibrillator having a plurality of use models each having associated therewith a characteristic power consumption time and duration, the device comprising:

a battery pocket constructed and arranged to receive and operate with an industry standard battery pack having a first battery chemistry and standard mechanical and electrical battery interfaces, and a customized battery pack having a second battery chemistry different than said first battery chemistry and a custom interface comprising said standard mechanical battery interface, said standard electrical battery interface and one or more distinguishing features different than said standard battery interface;

a battery chemistry identification system constructed and arranged to detect a presence or absence of said one or more distinguishing features and for generating a battery chemistry indication signal indicative of said battery chemistry of a battery pack installed in said battery pocket; and circuitry that adjusts the operation of the defibrillator to a use model appropriate for the battery pack inserted into the battery pocket.

2. The device of claim 1, wherein the device is a portable defibrillator.

3. The defibrillator of claim 1, further comprising:

a battery management system for managing said installed battery pack in accordance with said battery chemistry indication signal.

4. The defibrillator of claim 3, wherein said battery management system charges and discharges said installed battery pack in accordance with said use model and said battery chemistry of said installed battery pack.

5. The defibrillator of claim 1, wherein said first battery chemistry is lead acid that enables said industry standard battery pack to support reliable and efficient device operations in accordance with a first use model.

6. The defibrillator of claim 5, wherein said second battery chemistry is lithium (Li) that enables said customized battery pack to support reliable and efficient device operations in accordance with a second use model.

7. The defibrillator of claim 5, wherein said second battery chemistry is nickel cadmium (NiCd) that enables said customized battery pack to support reliable and efficient device operations in accordance with a second use model.

8. The defibrillator of claim 5, wherein said identification system comprises:

a sensing device constructed and arranged to detect a presence or absence of said distinguishing feature(s); and a controller operationally coupled to said sensing device for generating said battery pack chemistry identification signal based on said presence or absence of said distinguishing feature(s).

9. The defibrillator of claim 5, wherein said distinguishing feature is located on said standard mechanical interface of said customized battery pack.

10. The defibrillator of claim 5, wherein said distinguishing feature is located on said standard electrical interface of said customized battery pack.

11. The defibrillator of claim 1, wherein said first battery chemistry enables said industry standard battery pack to support reliable and efficient device operations in accordance with a first use model, and wherein said second chemistry enables said customized battery pack to support reliable and efficient device operations in accordance with a second use model.

12. The defibrillator of claim 1, wherein said standard electrical battery interface comprises a positive terminal and a negative terminal, and wherein said device includes corresponding contacts to electrically contact the battery pack terminals when said industry standard and said customized battery pack is installed in the device;

wherein said one or more distinguishing features comprises said negative terminal of said customized battery pack has a dimension different that said negative terminal of said industry standard battery pack;

wherein said sensing device comprises a third electrical contact disposed within the battery pocket constructed and arranged to distinguish between said negative terminal of said industry standard battery pack and said negative terminal of said customized battery pack when said customized battery pack is installed in said battery pocket.

13. The defibrillator of claim 1, wherein said standard electrical battery interface comprises a positive terminal and a negative terminal, and wherein said device includes corresponding contacts to electrically contact the battery pack terminals when said industry standard and said customized battery pack is installed in the device, and wherein said one or more distinguishing features comprises a third electrical terminal disposed on a surface of the customized battery pack, and wherein said sensing device comprises a third electrical contact disposed within the battery pocket constructed and arranged to contact said third electrical terminal when said customized battery pack is installed in said battery pocket.

14. The defibrillator of claim 13, wherein said third electrical contact and one of said positive or negative terminals form a unitary terminal, wherein said third contact is disposed immediately adjacent to said corresponding contact.

15. The defibrillator of claim 13, wherein said distinguishing feature comprises reflective coating position on said battery pack; and wherein said battery chemistry identification system comprises a photodetector constructed and arranged to detect said reflective coating when said customize battery pack is installed in said defibrillator.

16. A customized battery pack offering a different use model than an industry standard battery pack, the customized battery pack, comprising:

a mechanical interface substantially the same as that provided by a industry standard battery pack;

an electrical interface substantially the same as that provided by said industry standard battery pack;

a battery chemistry different than said industry standard battery pack; and one or more distinguishing features located on one of said mechanical and electrical interfaces, wherein said distinguishing features are not provided on said industry standard battery interface so as to indicate the use model appropriate to a device adapted to receive the customized battery pack, wherein said one or more distinguishing features includes a reflective coating positioned one of either mechanical or electrical interface to be detected by a photodetector located in the device adapted to receive the customized battery pack.

17. The battery pack of claim 16, wherein said battery chemistry of said industry standard battery pack is lead acid and wherein said battery chemistry of said custom battery pack is lithium.

18. The battery pack of claim 16, wherein said battery chemistry of said industry standard battery pack is lead acid and wherein said battery chemistry of said custom battery pack is nickel cadmium (NiCd).

* * * * *